United States Patent [19]
Williamson

[11] Patent Number: 5,842,976
[45] Date of Patent: Dec. 1, 1998

[54] DISPENSING, STORAGE, CONTROL AND INVENTORY SYSTEM WITH MEDICATION AND TREATMENT CHART RECORD

[75] Inventor: Michael J. Williamson, San Diego, Calif.

[73] Assignee: Pyxis Corporation, San Diego, Calif.

[21] Appl. No.: 648,580

[22] Filed: May 16, 1996

[51] Int. Cl.$^6$ ....................................................... A61B 5/00
[52] U.S. Cl. ................... 600/300; 128/920; 364/479.02; 364/479.07; 364/479.11
[58] Field of Search ............................ 128/630, 921–924, 128/920; 600/300; 364/479.02, 479.07, 479.11

[56] References Cited

U.S. PATENT DOCUMENTS

| | | | |
|---|---|---|---|
| 4,390,840 | 6/1983 | Ganssen et al. | 324/309 |
| 4,732,411 | 3/1988 | Siegel | 283/75 |
| 4,736,751 | 4/1988 | Gevins et al. | 128/731 |
| 4,793,355 | 12/1988 | Crum et al. | 324/248 |
| 4,839,806 | 6/1989 | Goldfischer et al. | 364/413.02 |
| 4,847,764 | 7/1989 | Halvorson et al. | 364/413.02 |
| 4,862,359 | 8/1989 | Trivedi et al. | 128/731 |
| 4,913,152 | 4/1990 | Ko et al. | 128/653 R |
| 4,940,058 | 7/1990 | Taff et al. | 128/653 R |
| 5,084,828 | 1/1992 | Kaufman et al. | 364/479 |
| 5,564,803 | 10/1996 | McDonald et al. | 312/215 |
| 5,597,995 | 1/1997 | Williams et al. | 235/375 |
| 5,623,242 | 4/1997 | Dawson, Jr. et al. | 340/311.1 |

FOREIGN PATENT DOCUMENTS

| | | | |
|---|---|---|---|
| 3725532 | 2/1989 | Germany | A61B 5/04 |
| 3735668 | 5/1989 | Germany . | |

OTHER PUBLICATIONS

V.O. Dossell & Kullman, "SQUIDS und Bilder Neuronaler Strome", Phys. Bl., 44, (1988) NR. 11, pp. 423–425.

M. Hoke, "SQUID–based Measuring Techniques — A Challenge For The Functional Diagnostics in Medicine", The Art of Measurement: Metrology in Fundamental & Applied Physics, pp. 287–335, 1st Edition: 1988.

W.J. Dallas, W.E. Smith, H.A. Schlitt, & W. Kullman, "Bioelectric Current Image Reconstruction From Measurement Of The Generated Magnetic Fields", Medical Imaging, SPIE, vol. 767, (1987), pp. 1–10.

B. Jeffs, R. Leahy & M. Singh, "An Evaluation of Methods for Neuromagnetic Image Reconstruction", IEEE Transaction on Biomedical Engineering, vol. BME–34, No. 9, Sep. 1987, pp. 713–723.

S. Ueno et al., "The MEG Topography and The Source Model of Abnormal Neural Activities Associated with Brain Lesions", IEEE Transactions on Magnetics, vol. Mag–22, No. 5, Sep. 1986, pp. 874–876.

*Primary Examiner*—Francis Jaworski
*Attorney, Agent, or Firm*—Michael D. Steffensmeier

[57] ABSTRACT

A system for monitoring, dispensing and reordering medication to patients who use patient-owned medication, including, in combination, a central site computer including device for receiving and storing therein data relevant to specific patients, their medical needs and the reorder sources of medication they require, at least one mobile charting computer, connected by radio frequency data link to the central site computer and including a central process unit to receive, store and process data received from the central site computer, an electronic camera for obtaining a picture of the patient and joining it with the patient's specific medical needs and his or her reorder sources of medication for storing in the central site computer and transmitting it on demand to the charting computer, and a monitor device connected to the charting computer to display the pertinent data on a specific patient as well as his or her electronic picture so that identification of the specific patient and his or her personal medical needs is confirmed.

27 Claims, 5 Drawing Sheets

System Block Diagram

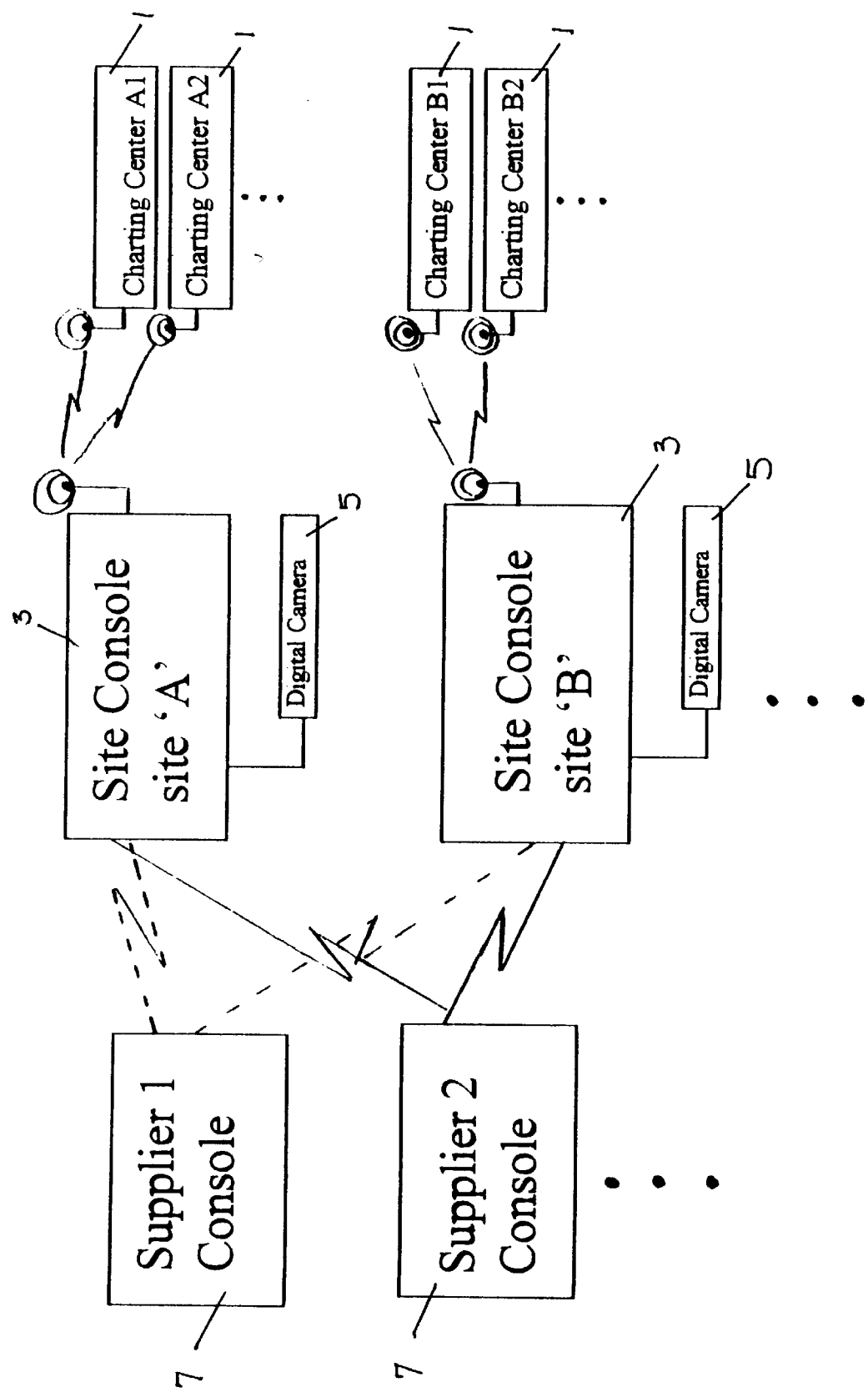
Figure 1 - System Block Diagram

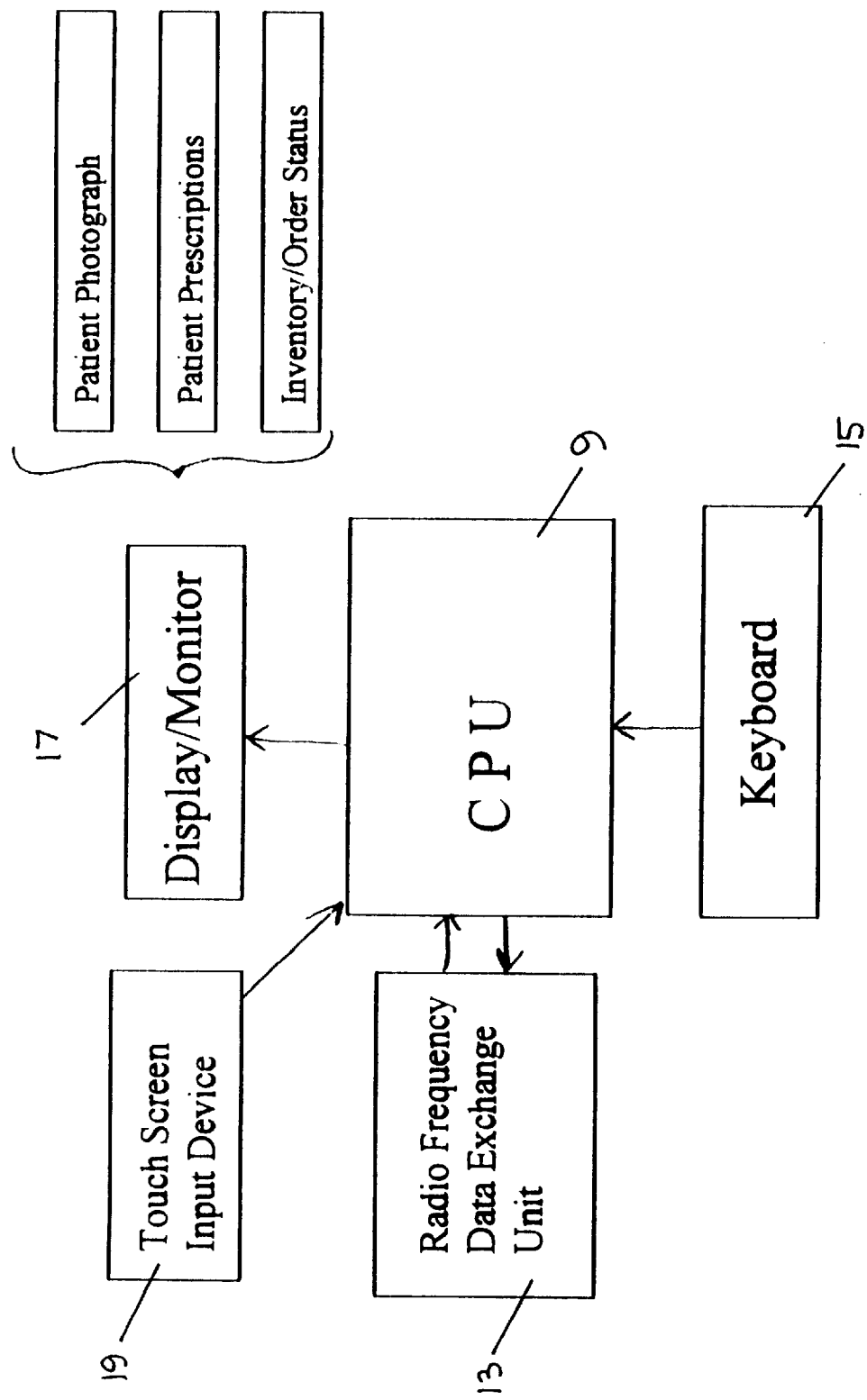

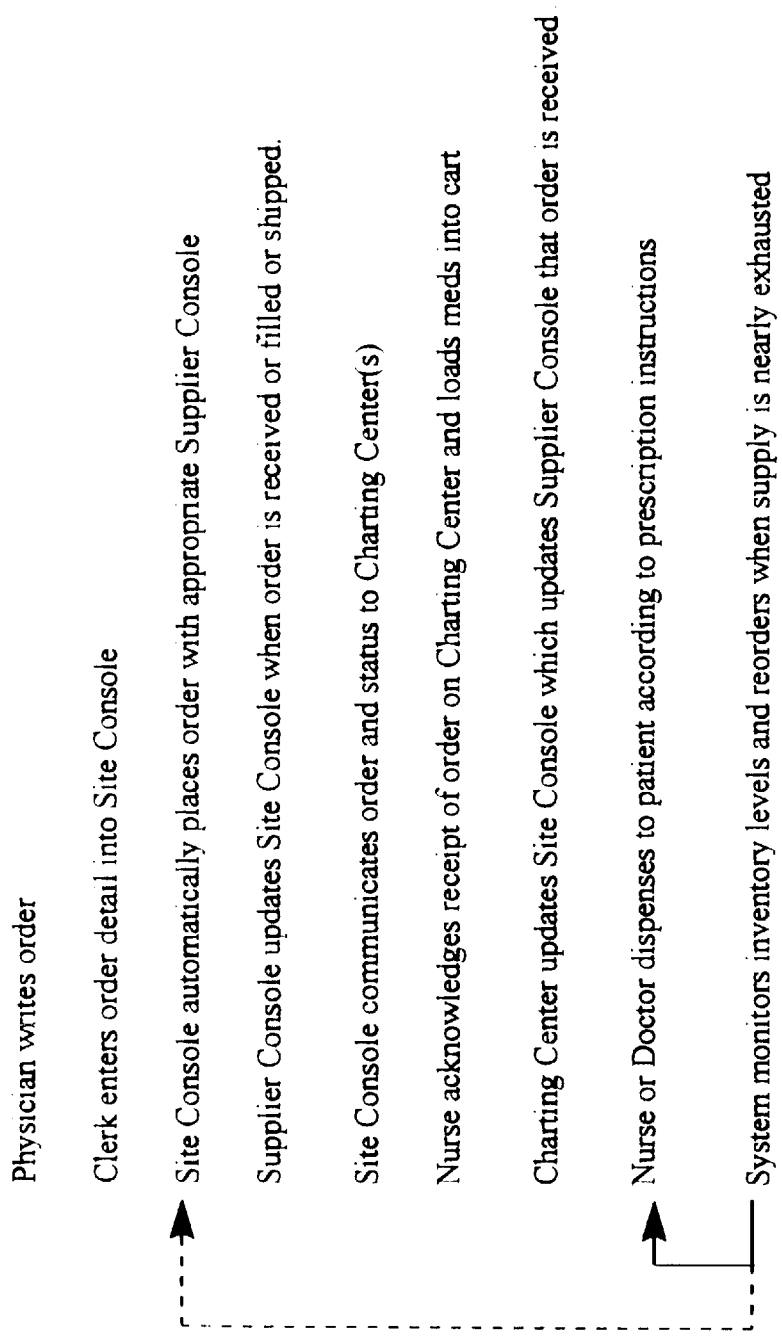

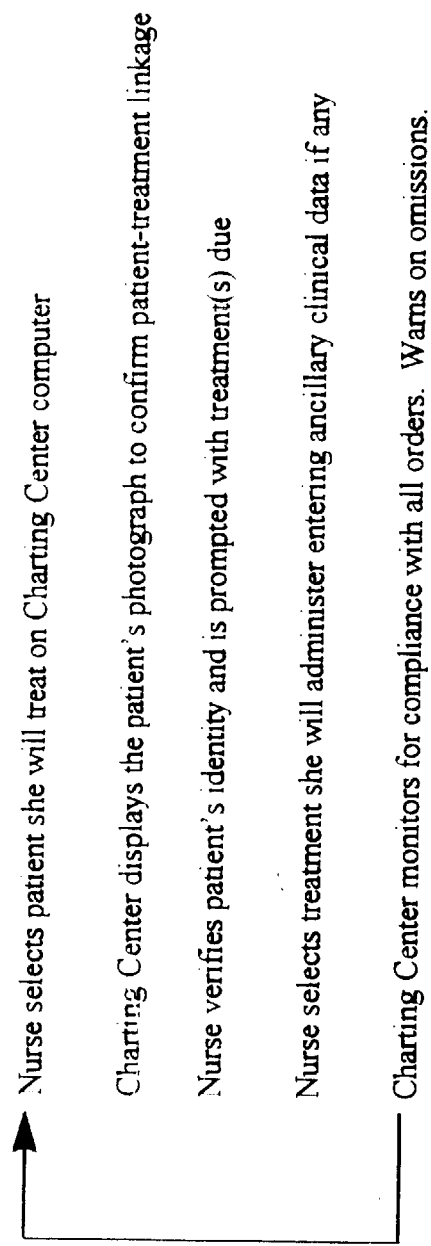
Figure 4 - Medication (treatment) administration

Figure 5 - Patient photograph propagation

Patient's face is photographed on admission to the nursing care area using a portable digital camera Portable digital camera is temporarily connected to the Site Console Computer by a cable Digitized patient photograph is transferred from camera to Site Console Computer Site Console stores the photograph locally Site Console Computer forwards photograph to Charting Centers via radio frequency data link

5,842,976

DISPENSING, STORAGE, CONTROL AND INVENTORY SYSTEM WITH MEDICATION AND TREATMENT CHART RECORD

BACKGROUND OF THE INVENTION

1. Field of the Invention

This invention relates generally to the means and procedure for storage, dispensing, inventorying and patient charting of medications and other medical treatments and equipment. More particularly, this invention relates to a computerized system of integrated means for medication control and inventory, as well as the visual linkage of a patient's image to his or her medical record.

2. Description of the Prior Art

Medical dispensing machines are well-known in the art. In medicine, the existence and use of dangerous narcotics and other medications have led to the development of machines and systems that allow for safe and effective control and monitoring of hospital medications with the least amount of time and inconvenience to the nursing, pharmacy, and physician staff of the facility. Nurses working in a hospital or other care facility must always be careful to record every use and application of medicine or other treatment to the patient. Even with care-giver diligence, there are circumstances which create the potential for error and omission of information in the patient record. In addition, the hospital staff must continually monitor levels of medications and communicate with the hospital pharmacy for resupply of medications.

These same problems exist in long-term care facilities along with additional problems specific to this setting. Whereas medicine supplies are generally owned by the hospital until administered, patients in long-term care facilities individually own all medications which are used on a regular basis. Furthermore, whereas resupply in a hospital generally occurs from one central store e.g. the hospital pharmacy, patients in long-term care facilities obtain their medicines from the supplier of their choosing. In the extreme case, this supplier may be different for each medication they require. At the long-term care facility these medications have to be monitored and reordered in a timely fashion. This creates three distinct problems for the long-term care facility. The first is the proper timing for reordering a medication. The second is the direction of an order to the correct source of resupply. The third is the segregation and control of patient-owned supplies and medications. These three problems differ from distribution and control problems in hospitals and require different automation systems to address them.

Whether a person is a short-term hospital patient or a long-term resident in a care facility, the potential for medication error is always a factor with which care facilities struggle. The potential for patients to receive the wrong medication is always an issue. Some patients may receive improper medications because they have changed rooms and their chart has not yet moved, or the chart has been misplaced, or mixed up with another patient's medical record. Although this is not an overwhelming cause of hospital error the potential for error is great enough to require further minimization of risk.

One such attempt to control the dispensing and storage of medication can be seen in U.S. Pat. No. 4,967,928 to Carter. This patent sets forth a means and a method for dispensing medicines including narcotics on the nursing unit floor. Carter discloses a cart wherein a computer is positioned. The computer has memory and various input devices such as a card reader, a keyboard, and a barcode reader. The cart has a cabinet linked to it which is divided into two sections, a locked section which houses narcotics and a second which houses other medications. The computer controls the output of medications, including narcotics, and maintains a tally on the used medicines. This system is effective to control access to medications and to reduce theft or loss of controlled substances, but its capabilities do not rise to the level of those of the claimed invention. Carter does not allow for monitoring of medications owned by the patient as would be required in an extended-care facility. Further, there is no mechanism of control or charting between the patient's record and the automated system. No automatic reordering exists in Carter's invention and there is no identifiable way to connect or reduce error in dispensing medicine to the patient.

In U.S. Pat. No. 3,917,045 to Williams et al., the invention includes a locked cabinet housing a plurality of removable and refillable cartridges. Each cartridge has the ability to store a plurality of individual, identical drug doses which can be sequentially dispensed on demand. The doses are dispensed in response to information input into the machine. Although Williams et al. discloses an apparatus which is effective in storing and dispensing, there is no mechanism to accurately protect against the error problems such as incorrect patient identification and reordering.

Thus, there remains a need for a medication dispensing system which not only controls the dispensing of dangerous narcotics, but controls the proper timing for reordering a medication, directs the order to the correct source of resupply, and segregates and controls patient-owned supplies and medication.

SUMMARY OF THE INVENTION

The invention is an automated medication monitoring, dispensing and reordering system which incorporates the ability to reduce error by presenting patient images on the system. Further, the invention includes the capability of monitoring and evaluating the medication inventories, to automate and optimize the reorder process, thereby reducing the financial burden on the user. The system includes a plurality of computers which are linked together to form a network. Said computers are capable of communicating together to provide the best and most effective method of monitoring a patient's medication needs as well as reducing the potential for human error and maintaining an accurate record of the patient's treatment and progress.

The system includes a mobile charting center computer which accompanies the nurse and mobile stores of patient-owned medications and supplies on medication or treatment rounds. This mobile charting center stays in communication with other system computers via a radio frequency data link. The mobile charting center computer is the primary input center for all patient activity such as medication usage. When a nurse extracts and administers medications or treatments, the activity is recorded in a mobile charting center memory and is communicated to other system computers. This electronic record allows the patient-owned medication stocks to be debited. The automated reorder process is triggered by a decrease in stock below a preset threshold level.

The system includes a site computer. This site computer has two main functions. First, it acts as an intermediary in the processing of prescriptions, and second as an archiving system for patient pictures and wound images. The site computer routes data including prescriptions and pictures to all devices within the network.

The system includes a supplier computer. It is capable of serving multiple facilities and is generally located at a supplier warehouse. The supplier computer receives resupply orders communicated from the charting center computers or site computers. Additionally, it provides a means for the supplier to input progress toward satisfying orders. Said progress is communicated to the charting center and site computers thereby eliminating the need for costly and time consuming telephone follow-up.

Any single system component is able to integrate with numerous other complementary components. This provides a system able to solve the complex resupply problems associated with the long-term care health delivery system.

Activity, usually by a nurse, at the charting center activates the reorder monitoring process by reducing the level of medication with each dosage. When a medication has been reduced below a predetermined point then the reorder process is activated. The system has been programmed to determine what that point is for each medication based on the type of prescription and the patient's requirement for that medication. When the charting activity brings a medication below said point, a reorder transaction is generated and is transmitted to the site computer. The site computer receives the order and routes that order to the correct supplier computer as well as the other charting centers in its area. The appropriate supplier is determined by factors, such as the patient's insurance provider, preferred vendor, type of supply or medication, and cost variance.

The supplier computer receives the request from the site computer and forwards the information to the supplier's host system. When the order is sent the supplier computer immediately receives the order status back from the supplier system and informs the correct facility of the order status so that the facility will know the order status at all times. When an order is filled the supplier's host informs the supplier computer of the impending delivery of the product. This information is forwarded to the site computer by the supplier computer. When the medication or supply is received by the facility, the nurse or other appropriate person, checks in the supply using the charting computer or site computer and closes out the request system-wide.

Images of the patient are incorporated into the system to reduce the potential for error when providing medication, as well as providing a tool whereby care-givers can quickly familiarize themselves with their patients and thereby promote a more comfortable and secure atmosphere for the patient. Such a system improves the overall experience of the patient in a facility. A digital camera is intermittently connected to the site computer to download patient images taken upon admission to the facility. The site computer then routes the image to all devices located within the network which maintains or has access to patient information. Thereafter, whenever a patient's record is brought to the screen the patient's photograph is displayed on the screen as well. Therefore, when a nurse or physician treats the patient he has a visual representation of that patient, on the charting computer, for reference.

In much the same way, a physician or nurse can use a digital camera attached to a charting computer to document a wound or injury. The care-giver takes a photograph using the digital camera. The time-stamped electronic photograph becomes part of the patient's record on the charting computer and is sent along to the site computer. The site computer similarly makes the photograph part of the patient's record. Such a system allows a care-giver to monitor the progress of a wound as it heals or conversely as it develops. Another benefit is that a nurse or doctor working an evening shift will be able to accurately document any changes that may occur to a patient throughout the night so that another doctor or nurse may view the exact change which occurred.

Other features and advantages of the invention will become apparent from the following detailed description, taken in conjunction with the accompanying drawings, which illustrate, by way of example, the features of the invention.

These and other objects of the invention will become more apparent when reading the description of the preferred embodiment along with the drawings that are appended hereto. The protection sought by the inventor may be gleaned from a fair reading of the claims that conclude this specification.

DESCRIPTION OF THE DRAWINGS

FIG. 1 is a schematic block diagram of the preferred embodiment of this invention;

FIG. 2 is a schematic diagram of the various parts of a typical charting center of this invention;

FIG. 3 is a flow chart of activities relating to inventory maintenance;

FIG. 4 is a flow chart of actions undertaken by nursing or physician personnel to dispense medicines or treatments during rounds according to the practices of this invention; and, FIG. 5 is a flow chart of activities relating to the image linkage to patient records according to the practices of this invention.

DESCRIPTION OF THE PREFERRED EMBODIMENTS

Turning now to the drawings, where like items are identified by like numerals and labels throughout the five figures, FIG. 1 shows the overall system of this invention to comprise at least one mobile charting computer 1, linked to a site computer 3 by radio telemetry, wherein said site computer 3 has attached thereto a digital camera 5 for use as will be hereinafter more fully explained. A plurality of supplier computers 7 are located, usually one in each warehouse or administration office of a medicine supplier, for the purpose of handling ordering and reordering of medicines to the particular system. Supplier computers 7 are preferably connected to site computer 3 by land lines or satellite communications.

In its preferred embodiment, one site computer 3 is located in the main office of an extended-care facility. Its function is to act as an intermediary in the processing of medicine prescriptions and as an archiving system for patient pictures and wound images. Upon admittance of a patient to an extended-care facility, all existing prescribed medicines are entered into the memory of site computer 3 along with the identification of patient-chosen medicine and supply sources, if any. Digital camera 5 is used to take a picture of the new patient and store the digitized picture in its memory unit along with transmitting the medicine and treatment schedule and picture to charting computer 1.

This invention is therefore embodied in a medication inventory, dispensing and reordering system which incorporates the use of visual images of the patient to provide more accurate care with a decreased possibility of dangerous care-giver error.

Charting computer 1 is shown in FIG. 2 to comprise a central processing unit (CPU) 9 that is fed information through a radio frequency data exchange unit 13, and includes a computer keyboard 15, a display monitor 17 and a touch screen input device 19 that allows the user to touch the screen at various locations to activate CPU 9 to undertake various operations such as mark a patient's chart as having a treatment completed or as having given the patient a dose of certain prescribed medicine. CPU 9 also includes a memory (not shown) integral therewith for retaining the appropriate patient photograph, patient prescriptions and medical inventory/order status that was inputted thereto through a radio frequency data link with site computer 3.

Charting computer 1 accompanies the nurse and mobile stores of patient-owned medications and supplies on medication or treatment rounds in the extended care facility. Mobile stores of patient-owned medications and supplies are already known in the art and a well-known example of such is disclosed in U.S. Pat. No. 5,014,875. This mobile store is computer-controlled and retains the medicines and supplies in locked storage to be dispensed under strict control and monitoring thereby providing greater accountability and more timely reordering.

According to generally accepted standards of care, when medications or supplies are administered to a patient the nurse makes a notation onto the patient's paper chart or record, indicating the exact nature of the medication or supply that was administered. Using the present invention, a nurse who provides a medication or supply to a patient, uses charting computer 1. Charting computer 1 requires certain information from the nurse namely nurse identification, password, and patient name before permitting access to the system's charting functions. After providing said required information the nurse may then review, administer, and document the required medication as directed by the patient's chart. Upon completion of this process, charting computer 1 enters the patient care information into the patient's file to indicate the medication was administered, and then updates the inventory list for that particular medication.

Within the aforementioned process, the nurse will note that upon accessing the patient's file there will be a photograph of the patient displayed on monitor 17 for proper identification. The photo identification will eliminate error particularly in the case of a new patient or when a nurse is new to that particular unit. The patient's photograph becomes part of the file when the patient is admitted into the hospital or long-term care facility. During the admission process digital camera 5 is used to take a photograph of the patient. Digital camera 5 is briefly connected to site computer 3 at the facility to transfer the digital image of the patient. Said site computer 3 thereafter routes said patient's photograph to other system components that communicate with said computer. Thereafter, whenever that patient's chart is called to the screen, at any of the charting computers 1 or site computer 3, the patient's photograph is displayed.

In much the same manner, the nurse or physician is able to use digital camera 5 to chart and monitor the treatment of a wound, injury or area of interest. The nurse may take a photograph of the wound using digital camera 5. To do so, digital camera 5 is briefly connected to charting computer 1 to download the image into the patient's record. Said charting computer 1 will first record the photograph and then communicate the photograph to site computer 3. Site computer 3 stores the image in the patient's file and communicates it to all other computers servicing that patient. Thereafter, anytime the file is displayed, the patient's photograph as well as the wound photograph may be displayed for viewing by the medical staff administering treatment at that time. Such a system can create an accurate history of the treatment a patient is given and the progress a wound makes as it is treated.

The benefits of such a system are numerous. Such a system will decrease the likelihood of malpractice claims because it will create an undisputed record of care as well as the development of a wound or injury. Similarly, a nurse or doctor is able to maintain an accurate record on which to seek other opinions by medical professionals who are called in to assist in a particular matter. The benefits to the patient are especially pronounced because a photographic monitoring system relieves the nurse or physician from a written description which can often be vague and may create confusion among care-givers as to what benefit a treatment is having or as to what progress has been made in the patient's care.

As shown in FIG. 3, this invention also contains a system for monitoring and reordering patient supplies and prescriptions. As shown, the physician writes an order for medicine to be administered to the patient. A clerk or other personnel enters this order in detail into site computer 3 where it remains in the memory subject to recall by appropriate personnel. A predetermined reorder point is set for each medication based upon the patient's needs, the type of medication, the quantity of reorder, and the specific supplier chosen by the patient or by the facility. Each time the nurse or administering personnel enters the data into charting computer 1, that accompanies the nurse along with a mobile medication store, and follows that with actually administering the medication, a software program in site computer 3 creates an entry which decreases the medication level toward the predetermined and programmed reorder point.

When the reorder point is reached, site computer 3 automatically places an order through land lines to supplier computer 7, located in the warehouse of the appropriate supplier. Supplier computer 7 notifies the appropriate personnel to fill the order while, at the same time, communicating with charting computer 1 to confirm the order and provide charting computer 1 with a status report on the order.

Upon receipt of the order of medicine at the facility, charting computer 1 notifies the nurse or person in charge and the medicine is loaded into the medications carried on the mobile store. The nurse signifies when the order has been loaded and charting computer 1 updates site computer 3 which updates supplier computer 7 that the order is received and terminating further reordering activity.

The nurse, doctor or other treating personnel then dispenses the medication to the patient according to prescriptions and instructions contained in charter computer and the patient is treated. The system begins monitoring anew and the process is repeated.

When a reorder message is sent by site computer 3 it is done so by radio telemetry. This method of data transmission is important in this part of the system for a number of reasons. First there is the rapidity at which the transmission is made. There may be other charting computers used in the facility and without such rapid transmission of data, there is a chance that another charting computer 1 will be moved into the same area with a different nurse who will re-administer the same medicine resulting in over-medication which has been the cause of some tragic accidents. The radio telemetry is instantaneous and does not require any sort of wires or plugs that would delay it on its rounds. In addition, there are no wires to drag on the floor when using radio telemetry so that the mobile store and charting computer 1 will be handled more safely.

When reorder information is sent to a specific supplier, previous arrangement has already been made to provide only certain information. This results in a savings of time and cost in not having to send a large amount of information that has to be processed into useful information and extraneous information that may cause a mix-up in the order. Extraneous information is not sent because the software program in the site computer already knows what information to send and what not to send.

The use of land lines to transmit these orders over radio telephone is for the purpose of saving costs in transmission. Many calls or orders can be made automatically at times when telephone service costs are minimized such as at night or during off-hours of operation. In addition, a plurality of orders to a specific supplier may be made with the resulting savings to the patient because of bulk ordering. This is important as many facilities are frequently geographically distant from suppliers making telecommunication costs important.

Site computer 3 informs all other charting computers 1 in its service area of the reorder procedure and can inform the facility's host administrative computer as well; this administrative computer may be tied into one or more health maintenance organizations that wish to be provided with up-to-date data on all of its clients in the facility. In this way, the entire network is updated with the reorder information, thereby reducing any likelihood of double ordering. When site computer 3 obtains the reorder request from charting computer 1, it forwards the information to the supplier's computer 7 and receives an order status back from the supplier. The order status is then transmitted from site computer 3 to site computer 3. Site computer 3 then updates all charting computers 3 within its network with the reorder status.

The system is capable of updating all orders status whenever it communicates with the supplier and subsequently transmits that information to site computer 3 which updates the complete network. Previous to this invention, nursing personnel checking on the status of reorders made numerous telephone calls to suppliers and, depending on the time zone in which the supplier was located, found it was difficult for accurate updating. This invention allows the nurse or other personnel at the charting computer to know the latest information on the status of the reorder at any given time and maintain his or her full attention on the patients.

When an order of medication or supplies is actually received in the facility, the nurse who restocks the mobile store accompanying charting computer 1 inputs the delivery information into the system and closes out the reorder request. That information is then routed to site computer 3 which updates the entire system.

As shown in FIG. 4, the nurse brings or rolls the mobile stores cabinet and charting computer 1 up to a patient's bedside. She selects the patient he or she will treat and brings up that patient's status on display monitor 17. Charting computer 1 then brings up the patient's digitized photograph and presents it on monitor 17 so that the nurse can cross-check that he or she has the appropriate chart for the selected patient.

The nurse then verifies the patient's identity and is prompted with the treatments scheduled for that period. He or she may then select the treatment he or she will administer to patent and enter any ancillary clinical data such as temperature, heart rate, etc.

The nurse then administers the appropriate medicine, taking it and whatever supplies he or she requires from the mobile store. As each treatment is completed, the nurse touches monitor 17 to engage touch screen input device 19 and provide an entry that this particular treatment is completed. Each dose of medicine administered at this time causes a debit on the balance of medicine on hand for this patient and begins to drive the inventory downward toward the previously set reorder point.

Charting computer 1 monitors the inputs from the nurse for compliance with all orders of the physician. Should the nurse attempt to close out the patient's chart without completing his or her duties, computer 1 provides him or her with an electronic warning that all administrations are not done and for him or her to continue until they are completed. Should the patient require a treatment not previously programmed, the nurse may use his or her own professional training to determine to provide this treatment and enter it into the record so that the facility, the doctor and any health maintenance organization may become aware of this added treatment and cost. Close control of medication and supplies provided to this patient is maintained while allowing the nurse to utilize his or her nursing skills for the betterment of the patient.

As shown in FIG. 5, the electronic photograph is a very important component in this inventive system. As shown, upon entry of the patient into the facility, he or she is photographed with digital camera 5 and the photo digitized into a stream of electronic bits that are sent to storage in the camera. At the present time, digital cameras are about the size of cellular telephones and use room lighting to take the picture. They are unobtrusive and the patient is not placed in any stressful situation.

Digital camera 5 then is temporarily connected to site computer 3 by a cable where the stored bits of energy making up the digitized picture are transmitted for storage. Camera 5 may be stored on site computer 3 or kept with charting computer 1. Site computer 3 then forwards the digitized photograph to each charting computer 1 by radio frequency data link. This means of transferring the image is necessary because the patient may already have been placed in a room and a nurse is standing by to proceed with an initial treatment. It has occurred that the wrong treatment is given to a patient. This radio frequency data link is instantaneous and will provide the nurse with a quick and efficient way of verifying the identity of the new admittee so that these mistakes do not occur.

When a patient is suffering from a wound, such as a bed sore, camera 5 is useful in taking pictures of the wound so that an accurate picture and history of pictures may be made and fed into charting computer 1 and maintained in the memory so that a real-time analysis may be made of the history of the development or treatment of the wound over time.

While the invention has been described with reference to a particular embodiment thereof, those skilled in the art will be able to make various modifications to the described embodiment of the invention without departing from the true spirit and scope thereof. It is intended that all combinations of elements and steps which perform substantially the same function in substantially the way to achieve substantially the same result are within the scope of this invention.

What is claimed is:

1. A system for monitoring, tracking dispensing, and reordering patient-specific medication from a supplier of the medication, and monitoring a patient's medical treatment and progress, at the point of care for patients, comprising in combination:

a) a central site computer including means for receiving and storing therein data relevant to specific patients, their needed medication, medical supplies, and treatments, and the reorder sources of medication they require;

b) at least one mobile charting computer connected by radio frequency data link to said central site computer and including a central process unit to receive, store and process data received from said central site computer;

c) an electronic camera for obtaining a picture of the patient and including said picture with the patient's specifically needed medication, medical supplies, and treatments, and his or her reorder sources of medication for storing in said central site computer and transmitting it on demand to said charting computer; and, d) a monitor connected to said charting computer to display said data relevant to specific patients, their needed medication, medical supplies, and treatments, and the reorder sources of medication they require, as well as their electronic picture so that identification of the specific patient and their needed medication, medical supplies, and treatments are confirmed.

2. The system of claim 1 further including a supplier computer for installation in each reorder source of medication for the patient, said computer being in electronic communication with said central site computer for receipt of reorders from said site computer when the available amount of medication for a specific patient reaches a preset minimum.

3. The system of claim 2 further including means in said supplier computer to send information back to said central site computer to confirm receipt of a reorder of medication and report the status of said reorder for broadcast as an update to each said mobile charting computer.

4. The system of claim 1 wherein said camera is a digital electronic camera that takes an electronic picture that is separatable into a stream of electronic bits that may be sent by radio frequency data link from said central site computer to said charting computer and reassembled to form a picture of the patient.

5. The system of claim 1 where said camera is a digital electronic camera connectible by cable to said charting computer to take pictures of wounds of patients in their bed and store each picture for later viewing by qualified personnel.

6. The system of claim 1 further including means for touch screen input of instructions to said monitor means to enable an attending nurse to request certain information and input instructions and data to said charting computer.

7. The system of claim 1 further including a mobile medication store for joinder with said mobile charting computer to allow the attending nurse to extract patient-specific medication therefrom for administering to the patient.

8. The system of claim 1, wherein said charting computer prompts a nurse about medical treatments scheduled during a certain period of time.

9. The system of claim 8, wherein said charting computer accepts input from the nurse about the scheduled medical treatments provided to the patient and ancillary clinical data.

10. The system of claim 1, wherein said charting computer accepts input from a nurse about any medical treatments given to the patient and any ancillary clinical data.

11. The system of claim 10, wherein the input accepted by said charting computer includes information that a medical treatment was completed and/or the patient was given a dose of a certain prescribed medicine.

12. A process of automatically monitoring, inventorying and reordering patient-specific medication from a supplier of the medication to the point of care of patients in a facility, comprising the steps of:

a) entering patient sources for resupply of medication into the memory of a central site computer;

b) establishing a set point of a minimum amount of patient-specific medication tolerated before reordering of said medicine is initiated;

c) transmitting said set point to a mobile charting computer that is moveable from patient to patient and storing said information therein;

d) administering said medication to a patient to whom treatment is indicated by said charting computer;

e) reducing the inventory by the amount and at the time each patient-specific medication is provided to the patient;

f) generating a reorder signal when the level of each patient-specific medication reaches said preset level and sending this reorder signal to said central site computer for re-sending to a computer located on the premises of the reorder source; and, g) monitoring the status of the reorder until delivery whereupon said medication is stored for later administration to the patient and said reorder signal is terminated.

13. The process of claim 12 wherein said step of entering patient sources for resupply of medication into the memory of a central site computer includes the additional step of entering patient medication and treatment information, pertaining to the particular patient, into said memory.

14. The process of claim 12 wherein said step of entering patient sources for resupply of medication into the memory of a central site computer is followed by the additional steps of obtaining an accurate electronic picture of the particular patient and reducing the picture to a stream of electronic bits that are storable in said computer memory.

15. The process of claim 14 wherein said steps of entering patient sources for resupply of medication into the memory of a central site computer, obtaining an accurate electronic picture of the particular patient, and reducing the picture to a stream of electronic bits that are storable in said computer memory are followed by the steps of transmitting said resupply information and said picture to a mobile charting computer that is moveable from patient to patient and storing said information and picture in a memory unit therein.

16. The process of claim 12 wherein said step of administering said medication to a patient to whom treatment is indicated by said charting computer is preceded by the step of confirming that the patient is the appropriate patient by comparison with the patient's photograph stored in said computer.

17. A process of automatically monitoring, inventorying and reordering patient-specific medication from a supplier of the medication to the point of care of patients in a facility, comprising the steps of:

a) entering patient medication and treatment information into the memory of a central site computer along with the particular sources for resupply of same;

b) obtaining an accurate electronic picture of the patient including reducing the picture to a stream of electronic bits that are storable in said computer memory;

c) instantaneously transmitting, by radio frequency data transmission, said patient information and said picture to a mobile charting computer that is moveable from patient to patient and storing said information and picture in a memory unit therein;

d) establishing a set point of a minimum amount of patient-owned medication tolerated before reordering of said medicine is initiated;

e) administering said medication to a patient to whom treatment is indicated by said charting computer and is confirmed by comparison with the photograph stored in said computer;

f) reducing the inventory by the amount and at the time each patient-owned medication is provided to the patient;

g) generating a reorder signal when the level of patient-owned medication reaches the preset level and sending this reorder signal to said central site computer for re-sending by electronic communication to a computer located on the premises of the reorder source; and, h) monitoring the status of the reorder until delivery whereupon said medication is stored for later administration and said reorder signal is terminated.

18. A system for monitoring, tracking dispensing, and reordering patient-specific medication from a supplier of the medication, and monitoring a patient's medical treatment and progress, at the point of care for patients, comprising in combination:

a) a central site computer including means for receiving and storing therein data relevant to specific patients, their needed medication, medical supplies, and treatments, and the reorder sources of medication they require;

b) at least one mobile charting computer, connected by radio frequency data link to said central site computer and including a central process unit to receive, store and process data received from said central site computer;

c) a monitor connected to said charting computer to display said data relevant to specific patients, their needed medication, medical supplies, and treatments, and the reorder sources of medication they require, the pertinent data on a specific patient as well as their electronic picture so that identification of the specific patient and their needed medication, medical supplies, and treatments are confirmed; and, d) a computer for installation in each reorder source of medication for the patient, said computer being in electronic communication with said central site computer for receipt of reorders from said site computer when the available amount of medication for a specific patient reaches a preset minimum.

19. The system of claim 18 further including an electronic camera for obtaining a picture of the patient and including said picture with the patient's specifically needed medication, medical supplies, and treatments, and his or her reorder sources of medication for storing in said central site computer and transmitting it on demand to said charting computer.

20. The system of claim 19 wherein said camera is a digital electronic camera that takes an electronic picture that is separatable into a stream of electronic bits that may be sent by radio frequency data link from said central site computer to said charting computer and reassembled to form a picture of the patient.

21. The system of claim 19 where said camera is a digital electronic camera connectible by cable to said charting computer to take pictures of wounds of patients in their bed and store each picture for later viewing by qualified personnel.

22. The system of claim 18 further including means for touch screen input of instructions to said monitor means to enable an attending nurse to request certain information and input instructions and data to said charting computer.

23. The system of claim 18 further including a mobile medication store for joinder with said mobile charting computer to allow the attending nurse to extract patient-specific medication therefrom for administering to the patient.

24. The system of claim 18 further including means in said supplier computer to send information back to said central site computer to confirm receipt of a reorder of medication and report the status of said reorder for broadcast as an update to each said mobile charting computer.

25. The system of claim 18, wherein said charting computer prompts a nurse about medical treatments scheduled during a certain period of time.

26. The system of claim 25, wherein said charting computer accepts input from the nurse about the scheduled medical treatments provided to the patient and ancillary clinical data.

27. The system of claim 26, wherein the input accepted by said charting computer includes information that a medical treatment was completed and/or the patient was given a dose of a certain prescribed medicine.

* * * * *